United States Patent [19]
Van Rees

[11] Patent Number: 6,083,456
[45] Date of Patent: Jul. 4, 2000

[54] AIR FRESHENER

[75] Inventor: Norman A. Van Rees, Kirkwood, Mo.

[73] Assignee: Chemia, Inc., Maryland Heights, Mo.

[21] Appl. No.: 08/058,092

[22] Filed: May 6, 1993

Related U.S. Application Data

[63] Continuation-in-part of application No. 07/882,272, May 13, 1992, abandoned.

[51] Int. Cl.⁷ ........................................................ A61L 9/00
[52] U.S. Cl. .......................... 422/5; 424/76.2; 536/102; 521/50
[58] Field of Search ........................ 422/5, 122, 305; 424/76.2, 76.7, 76.8; 426/578, 661; 239/60; 536/102; 521/50

[56] References Cited

U.S. PATENT DOCUMENTS

| | | | |
|---|---|---|---|
| 2,691,615 | 10/1954 | Turner et al. | 424/76.3 |
| 3,490,742 | 1/1970 | Nichols et al. | 426/578 |
| 4,339,550 | 7/1982 | Palinczar et al. | 521/99 |
| 4,369,308 | 1/1983 | Trubiano | 426/578 |
| 4,666,671 | 5/1987 | Purzycki et al. | 422/5 |
| 4,719,040 | 1/1988 | Traas et al. | 512/4 |
| 4,755,377 | 7/1988 | Steer | 239/60 |
| 4,770,710 | 9/1988 | Friedman et al. | 536/102 |
| 4,812,445 | 3/1989 | Eden et al. | 424/484 |
| 4,985,082 | 1/1991 | Whistler | 536/102 |

FOREIGN PATENT DOCUMENTS 0486630  5/1976  Australia ................................... 422/5

*Primary Examiner*—Laura Edwards
*Attorney, Agent, or Firm*—Armstrong Teasdale LLP

[57] ABSTRACT

A biodegradable air freshener that breaks down in the presence of water to minimize solid waste, comprising a water soluble substrate substantially comprising foamed vegetable starch, and a liquid fragrance carried in the substrate. The substrate is preferably made of corn and or potato starch. The liquid fragrance may be from about 0.01 to about 10 times the weight of the substrate. A coloring agent may optionally be provided in the liquid fragrance to impart color to the air freshener. Because the substrate is made from a water soluble starch, it dissolves in water leaving little or no solid waste.

16 Claims, 1 Drawing Sheet

_US 6,083,456_

AIR FRESHENER

CROSS-REFERENCE TO RELATED APPLICATION

This application is a continuation-in-part of U.S. patent application Ser. No. 07/882,272 filed May 13, 1992 now abandoned.

BACKGROUND AND SUMMARY OF THE INVENTION

This invention relates to air fresheners, odor masks and malodor neutralizers and, in particular, to a biodegradable air freshener that dissolves in water, leaving minimal solid waste.

Various types of air fresheners have been made to dispense fragrances and scents to mask or neutralize unpleasant odors or to simply provide a pleasant scent. One type of air freshener involves dissolving a fragrance in a liquid carrier, such as kerosene, or some other volatile organic compound. Fragrances may also be dissolved in water, although it is often necessary to use a detergent or other emulsifying agent to agent to dissolve the fragrance. The fragrance evaporates with the carrier, scenting the air. Liquid air fresheners are effective, but there is a risk of spillage. Moreover, there are concerns about the amount of volatile chemicals that are released and about disposal of the containers for the air freshener.

Sometimes fragrances are infused into a solid carrier, such as a fiber or polymer felt, or a polymer foam carrier such as a polyurethane or polystyrene foam. These solid carriers reduce the risk of spillage and help to control the rate of fragrance release. Moreover, the solid carriers can be incorporated into fan-driven air fresheners facilitating the release of the fragrance. However, these solid substrates are undesirable from an environmental viewpoint because of the potential disposal problems. Polyurethane and polystyrene are substantially non-biodegradable and will not decompose. Thus, after their useful life these air fresheners contribute to the solid waste disposal problem, becoming a permanent part of a landfill.

The present invention relates to an improved air freshener and odor neutralizer and the method of manufacturing the improved air freshener. Generally, the air freshener, according to the present invention, comprises a water soluble substrate made from a foamed vegetable starch. The substrate is impregnated with a liquid fragrance that can evaporate from the substrate to freshen the surrounding air or add fragrance. However, because the substrate is comprised of a foamed vegetable starch, it is water soluble and quickly breaks down when exposed to water. This not only reduces volume of solid waste that must be disposed of, but allows the spent air freshener to be conveniently disposed of in a sink or toilet. As the foam substrate dissolves, residual fragrance is released to freshen the sink or toilet. Because the substrate comprises substantially vegetable starches, the decomposition products are not harmful.

According to the method of making an air freshener according to this invention, water soluble foamed vegetable starch particles are provided. These particles are treated with a liquid fragrance and optionally a coloring agent, that is absorbed by the particles.

Thus, the air freshener of the present invention provides a ready, spill-proof source of fragrance to mask unpleasant odors or simply provide a pleasant scent. The air freshener provides controlled, long-lasting release of the fragrance. When the air freshener is spent, it is conveniently and completely disposable in a sink or toilet, where any residual fragrance freshens the sink or toilet. Even if the air freshener is disposed of by conventional means, it quickly breaks down when exposed to water and, therefore, does not take up space in landfills.

These and other features and advantages will be in part apparent and in part pointed out hereinafter.

DETAILED DESCRIPTION OF THE PREFERRED EMBODIMENT

An air freshener according to the principles of this invention comprises a water soluble substrate substantially comprising a foamed vegetable starch. The starch is preferably corn starch, potato starch or some combination of corn starch and potato starch. Of course, other suitable vegetable-derived starches could be used in addition to or instead of corn and/or, potato starches. One suitable substrate material is BIO PAC™ Responsible Loose Fill Packaging from EverGreen Solutions, Inc., Minneapolis, Minn. Another suitable substrate material is ECO-FOAM™ extruded foam from American Excelsior, Inc., Arlington, Tex. These materials are substantially dry, rigid, open-celled foams consisting essentially of vegetable starches.

ECO-FOAM™ is composed of over 95% cornstarch from a special high-amylose hybrid corn which meets FDA food grade regulations, and due to the high starch content it decomposes easily in water. The remaining ingredient is a water-soluble organic polymer which meets FDA food contact regulations, and is a common ingredient in adhesives, textiles, and paper coatings. ECO-FOAM™ is manufactured with an extruder in a simple heat and steam process, and generally resembles poly styrene foam. The ECO-FOAM™ can be formed into chips or pieces, generally resembling polystyrene packing peanuts, or ECO-FOAM can be formed into larger wafers and blocks, resembling polystyrene blocks.

Figure 1:
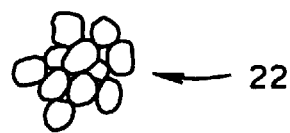
FIG. 1 is a drawing of water soluble foamed vegetable starch particles suitable for use as a substrate for an air freshener in accordance with this invention.
Figure 2:
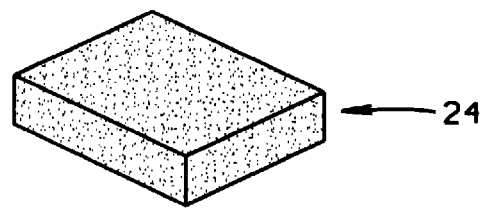
FIG. 2 is a drawing of a water soluble foamed vegetable wafer suitable for use as a substrate for an air freshener in accordance with this invention.
Figure 3:
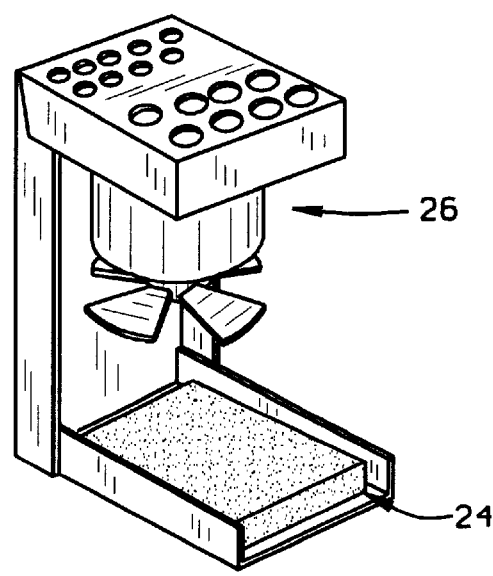
FIG. 3 is a perspective view of a fan-driven air freshener unit.

In contrast to plastic felts and foams which are made from petroleum, the foamed starch substrate is a readily renewable resource. The substrate can be in the form of a foam sheet or other specific shape, for example, the substrate may be in the form of particles or chips 22, shown in FIG. 1. Alternatively, the substrate may be in the form of a wafer 24, shown in FIG. 2, for use with a fan-driven air freshener 26 shown in FIG. 3.

A liquid fragrance is infused into the substrate. Because of the foamed form of the substrate, the substrate readily absorbs between about 0.01 and about 10 times its weight in fragrance. The amount of fragrance used depends upon the strength of the scent and its rate of release from the substrate. In a household application an appropriate light "potpourri"-type fragrance may be used. In an industrial or institutional application, such as a public restroom, a strong, effective odor neutralizing fragrance may be used. The liquid fragrance is preferably an anhydrous or nearly anhydrous liquid selected from the group of essential oils, aroma chemicals, and odor neutralizers and masks. The liquid fragrance is preferably, but not necessarily, a biodegradable substance.

A coloring agent can also be added to the liquid fragrance to impart color to the air freshener. The color, like the fragrance, is preferably, but not necessarily, a biodegradable substance.

The air freshener can be used in a forced-air air handling system to freshen or neutralize malodors. The air freshener can also be used as a potpourri or mixed with dried flowers, herbs and spices as part of a potpourri. Because of its low density the air freshener inexpensively adds desirable bulk to the potpourri. The air freshener is particularly well-suited for use in a simmering pot potpourri, since it can dissolve completely in water releasing fragrance into the water.

The air freshener can be stored in air tight containers or packages indefinitely, for example, in a high density polyethylene package. The useful life of the air freshener can be controlled by the inherent volatility of the fragrance components, the amount of fragrance absorbed into the substrate, the shape and surface area of the substrate, the air flow over the substrate and the ambient temperature and humidity. The amount and type of fragrance and the size and shape of the substrate can be selected to achieve the desired rate of fragrance release and air freshener life. To cover strong malodors fragrances that quickly volatize would be selected; to merely scent the air fragrances that volatilize slowly would be selected.

Because the foamed starch substrate is water soluble, when the useful life of the air freshener is over, the substrate can simply be thrown away. As soon as the substrate is exposed to water, it will dissolve, leaving no solid residue behind. The resulting decomposition products are not harmful. Preferably, however, the air freshener can be disposed of in a sink or toilet. The substrate dissolves immediately upon contact with the water, releasing any residual fragrance, which has the added benefit of freshening the sink or toilet. Thus disposal is easy, and environmentally responsible.

According to the method of this invention, a water soluble foamed starch substrate is provided. The substrate can be in the form of individual particles, a flat sheet, or any other convenient shape. The substrate is infused with a liquid fragrance, selected so that the liquid does not detrimentally dissolve the substrate.

EXAMPLE 1

The following is an example of the method of manufacturing air freshener according to this invention. 45.4 kilograms (100 pounds) of foamed vegetable starch BIO PAC™ Responsible Loose Fill Packaging chips from EverGreen Solutions, Inc., Minneapolis, Minn., with a typical chip size of 3.2 mm×6.4 mm×6.4 mm, are loaded into a 72 cubic foot (2 cubic meter) Marion Ribbon Blender. 136 kilograms (300 pounds) of Chemia Lemon Fragrance #3053, available from the Chemia Corporation, St. Louis, Mo., and 68 grams (0.15 pounds) of FD&C Yellow #11 are mixed in a 55 gallon (208 liter) stainless steel drum. The Ribbon Blender is started and the fragrance/dye mixture is sprayed onto the chips through a fine tip atomizer nozzle. The chips are mixed for five minutes until the solution is completely absorbed and the color is uniform. This imparts a pleasant lemon scent to the chips. The chips can be placed in an open container, to provide odor control or scent to a room as the liquid fragrance evaporates, or used in a simmering pot. When the scent has dissipated to the extent that it is no longer effective, the air freshener can be disposed of in the trash, where it dissolves on contact with water so that it does not add volume to a landfill, or more preferably the air freshener is dumped in a sink or toilet, where it dissolves releasing any remaining lemon fragrance to freshen the sink or toilet.

In view of the above, it will be seen that the several objects of the invention are achieved and other advantageous results attained.

As various changes could be made in the above constructions without departing from the scope of the invention, it is intended that all matter contained in the above description or shown in the accompanying drawings shall be interpreted as illustrative and not in a limiting sense.

What is claimed is:

1. A biodegradable air freshener and odor neutralizer that breaks down in the presence of water to minimize solid waste, the air freshener comprising:

a water soluble substrate substantially comprising a substantially dry, rigid, open-celled foam consisting essentially of vegetable starch; and a liquid fragrance carried in the substrate.

2. The air freshener according to claim 1 wherein the water soluble substrate comprises at least one of the group comprising corn starch and potato starch.

3. The air freshener according to claim 1 wherein the liquid fragrance comprises 0.01 to 10 times the weight of the substrate.

4. The air freshener according to claim 1 further comprising a coloring agent in the liquid fragrance carried in the substrate to impart color to the air freshener.

5. The air freshener according to claim 1 wherein the substrate is in the form of chips.

6. The air freshener according to claim 1 wherein the liquid fragrance is an anhydrous or nearly anhydrous liquid selected from the group of essential oils, aroma chemicals, and odor neutralizers and masks.

7. A method of making an air freshener comprising the steps of:

providing a water soluble substrate made of a substantially dry, rigid, open-celled foam consisting essentially of vegetable starch; and introducing liquid fragrance to be absorbed into the substrate.

8. The method according to claim 7 wherein the liquid fragrance is between 0.01 and 10 times the weight of the substrate.

9. The method according to claim 7 wherein the substrate comprises at least one of the group comprising corn starch and potato starch.

10. A biodegradable freshener and odor neutralizer product that breaks down in the presence of water to minimize solid waste, the freshener comprising:

a water soluble substrate made of a substantially dry, rigid, open-celled foam consisting essentially of vegetable starch; and a liquid, evaporatable fragrance carried in the substrate, which evaporates from the substrate to freshen air;

the substrate being completely dissolvable in water so that it can be disposed of down a sink or toilet, whereupon residual freshener will be released to freshen the sink or toilet.

11. The biodegradable freshener according to claim 10 wherein the water soluble substrate comprises at least one of the group comprising corn starch and potato starch.

12. The biodegradable freshener according to claim 10 wherein the liquid fragrance comprises 0.01 to 10 times the weight of the substrate.

13. The biodegradable freshener according to claim 10 further comprising a coloring agent in the liquid fragrance carried in the substrate to impart color to the household freshener.

14. The biodegradable freshener according to claim 10 wherein the substrate is in the form of chips.

15. The biodegradable freshener according to claim 10 wherein the liquid fragrance is an anhydrous or nearly anhydrous liquid selected from the group of essential oils, aroma chemicals, and odor neutralizers and masks.

16. A method of freshening the air comprising the steps of:

providing a substrate made of a substantially dry, rigid, open-celled foam consisting essentially of vegetable starch, infused with a volatile fragrance wherein the fragrance volatilizes;

from the substrate to freshen the surrounding air; and dissolving the substrate in water when the fragrance has substantially volatilized.

* * * * *